United States Patent
Ringemann et al.

(10) Patent No.: US 11,280,756 B2
(45) Date of Patent: Mar. 22, 2022

(54) METHOD FOR DETECTING AN INTERFERENT CONTRIBUTION IN A BIOSENSOR

(71) Applicant: Roche Diabetes Care, Inc., Indianapolis, IN (US)

(72) Inventors: Christian Ringemann, Mannheim (DE); Herbert Wieder, Lampertheim (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 723 days.

(21) Appl. No.: 16/082,154

(22) PCT Filed: Mar. 14, 2017

(86) PCT No.: PCT/EP2017/055919
§ 371 (c)(1),
(2) Date: Sep. 4, 2018

(87) PCT Pub. No.: WO2017/157894
PCT Pub. Date: Sep. 21, 2017

(65) Prior Publication Data
US 2019/0079044 A1    Mar. 14, 2019

(30) Foreign Application Priority Data

Mar. 14, 2016 (EP) .................................. 16160136

(51) Int. Cl.
*A61B 5/145* (2006.01)
*G01N 27/327* (2006.01)
*C12Q 1/00* (2006.01)

(52) U.S. Cl.
CPC ......... *G01N 27/327* (2013.01); *A61B 5/1451* (2013.01); *A61B 5/14532* (2013.01);
(Continued)

(58) Field of Classification Search
CPC .............. G01N 27/327; G01N 27/3274; A61B 5/1451; A61B 5/14532; A61B 5/14546; C12Q 1/006
(Continued)

(56) References Cited

U.S. PATENT DOCUMENTS

| 4,396,464 A | 8/1983 | Giner et al. |
| 6,121,009 A | 9/2000 | Heller et al. |

(Continued)

FOREIGN PATENT DOCUMENTS

| EP | 1 839 571 | 10/2007 |
| EP | 2 267 149 A1 | 12/2010 |

(Continued)

OTHER PUBLICATIONS

Search Report for related applicaiton 2018135164 mailed by the Russian Patent Office dated Jul. 9, 2019.
(Continued)

*Primary Examiner* — Navin Natnithithadha
(74) *Attorney, Agent, or Firm* — Woodard, Emhardt, Henry, Reeves & Wagner LLP

(57) ABSTRACT

A method for detecting an interferent contribution in a biosensor is disclosed. Herein, the biosensor has a first electrode (112), a second electrode, and a third electrode (114), wherein the first electrode (112) and the second electrode are covered by a membrane, wherein the first electrode (112) further includes an enzyme or wherein the first electrode (112) is covered by an enzyme layer. Further, the first electrode (112), the second electrode, and the third electrode (114) are connected via a potentiostat, wherein, in a normal operational mode, via the potentiostat an electrical potential difference is applied between the first electrode (112) and the second electrode in a manner that the first electrode (112) allows for oxidative processes and the third electrode (114) allows for reductive processes. The method comprises the steps of:

a) switching from the normal operational mode to an interferent detection mode, wherein, in the interferent detection mode, the electrical potential difference between the first electrode (112) and the second elec-
(Continued)

trode is altered for a limited period of time in a manner that the third electrode (114) allows for oxidative processes;
b) measuring a current-voltage characteristic (110) of the third electrode (114); and
c) determining the interferent contribution in the biosensor by evaluating the current-voltage characteristic (110) of the third electrode (114).

The method allows deducting the presence and, preferably, the amount of the interferent in an unambiguous way and is, generally, applicable in case of more than one kind of interferent. Neither additional working electrodes nor supplementary circuit components are required. The method is implementable within sensor electronics architectures of standard biosensors and, thus, applicable in already existing biosensor systems.

18 Claims, 7 Drawing Sheets

(52) U.S. Cl.
CPC .......... *A61B 5/14546* (2013.01); *C12Q 1/006* (2013.01); *G01N 27/3274* (2013.01)

(58) Field of Classification Search
USPC .......................................... 600/309, 345–366
See application file for complete search history.

(56) References Cited

U.S. PATENT DOCUMENTS

| | | |
|---|---|---|
| 6,863,800 B2 | 3/2005 | Karinka |
| 7,081,195 B2 | 7/2006 | Simpson et al. |
| 7,653,492 B2 | 1/2010 | Davies et al. |
| 7,896,809 B2 | 3/2011 | Simpson et al. |
| 2008/0000780 A1 | 1/2008 | Tonks |
| 2014/0158552 A1 | 6/2014 | Fujiwara et al. |

FOREIGN PATENT DOCUMENTS

| | | |
|---|---|---|
| RU | 2305279 | 6/2007 |
| WO | WO 98/36270 | 8/1998 |
| WO | WO 2016/030346 A2 | 3/2016 |

OTHER PUBLICATIONS

Office Action and Search Report in related CN201780017438.2 dated Jul. 8, 2020.

METHOD FOR DETECTING AN INTERFERENT CONTRIBUTION IN A BIOSENSOR

FIELD OF THE INVENTION

The present invention relates to a method for detecting an interferent contribution in a biosensor as well as to a related method for validating an operation of a biosensor and/or for calibrating the biosensor. The methods according to the present invention may primarily be used for a long-term monitoring of an analyte concentration in a body fluid, in particular for long-term monitoring of a blood glucose level or of the concentration of one or more other types of analytes in a body fluid. The invention may both be applied in the field of home care as well as in the filed of professional care, such as in hospitals. However, other applications are feasible.

RELATED ART

Monitoring certain body functions, more particularly monitoring one or more concentrations of certain analytes, plays an important role in the prevention and treatment of various diseases. Without restricting further possible applications, the invention is described in the following with reference to glucose monitoring in an interstitial fluid. However, the invention can also be applied to other types of analytes. Blood glucose monitoring may, specifically, be performed by using electrochemical biosensors besides optical measurements. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to "spot measurements" in which a sample of a body fluid is taken from a user, i.e. a human or an animal, in a targeted fashion and examined with respect to the analyte concentration, continuous measurements have become increasingly established. Thus, in the recent past, continuous measuring of glucose in the interstitial tissue, also referred to as "continuous glucose monitoring" or abbreviated to "CGM", has been established as another important method for managing, monitoring, and controlling a diabetes state. Herein, an active sensor region is applied directly to a measurement site which is, generally, arranged in an interstitial tissue, and may, for example, convert glucose into an electrically charged entity by using an enzyme, in particular glucose oxidase, generally abbreviated to "GOD". As a result, the detectable charge may be related to the glucose concentration and can, thus, be used as a measurement variable. Examples of such transcutaneous measurement systems are described in U.S. Pat. No. 6,360,888 B1 or US 2008/0242962 A1.

Typically, current continuous monitoring systems are transcutaneous systems or subcutaneous systems. Accordingly, the actual biosensor or at least a measuring portion of the biosensor may be arranged under the skin of the user. However, an evaluation and control part of the system, which may also be referred to as a "patch", may, generally, be located outside of the body of a user. Herein, the biosensor is generally applied by using an insertion instrument, which is, in an exemplary fashion, described in U.S. Pat. No. 6,360,888 B1. However, other types of insertion instruments are also known. Further, a control part may, typically, be required which may be located outside the body tissue and which has to be in communication with the biosensor. Generally, communication is established by providing at least one electrical contact between the biosensor and the control part, wherein the contact may be a permanent electrical contact or a releasable electrical contact. Other techniques for providing electrical contacts, such as by appropriate spring contacts, are generally known and may also be applied.

In continuous glucose measuring systems, the concentration of the analyte glucose may be determined by employing an electrochemical sensor comprising an electrochemical cell having at least a working electrode and a counter electrode. Herein, the working electrode may have a reagent layer comprising an enzyme with a redox active enzyme co-factor adapted to support an oxidation of the analyte in the body fluid. However, the body fluid may, further, comprise additional redox active substances which may be oxidized in a similar manner and may, thus, generate further electrons which may be detectable as an additional current, also be denoted by the terms "background current" or "zero current". In general, the additional redox active substances which may be present in the body fluid and are, thus, capable of influencing this kind of measurement are usually denominated as "interferents". On one hand, a first kind of interferents may behave in the same manner as the redox mediator and can, thus, directly be oxidized at the working electrode, thereby providing the additional current. On the other hand, a second kind of interferents may react with an intermediate product, such as hydrogen peroxide ($H_2O_2$) which is present in the case of a glucose reaction, whereby the concentration of the intermediate product in the body fluid may decrease, which may result in a diminished sensitivity of the amperometric measurement device.

As a result of the presence of one or more interferents within the body fluid, measuring errors of unknown magnitude may occur due to the additional current in a glucose sensor. By way of example, in some kinds of biosensors, large measuring errors may particularly occur at a beginning of a measuring sequence. Similar consequences may occur during the entire operation of factory-calibrated biosensors, wherein fixed values are, generally, provided for the background current. Thus, an alteration of the background current may easily result in a measuring error.

Hitherto, a number of technical solutions have been provided which might be able to reduce the effect of the interferents comprised in the body fluid onto the biosensor.

Firstly, it has been proposed to employ an interferent membrane, i.e. a membrane which is selective to the analyte and, concurrently, provides a barrier effect to the interferent. Thus, the interferent membrane may be capable of distinguishing between the analyte and the interferent in a manner that, preferably, only the analyte may reach the biosensor or at least the analyte detecting unit therein. Since most known interferent membranes comprise anionic groups intended to achieve an electrostatic repulsion of anionic interferents, it is, generally, not possible to completely inhibit the effect of all interferents.

Secondly, it may be feasible to provide a redox mediator which may comprise a low working potential. Accordingly, the value of the electrical potential at which the redox mediator can be oxidized may be lower than the value of the electrical potential at which an oxidation process of known interferents in body fluids may occur. However, this kind of modification typically requires an adapted concept for the operation of the biosensor and is, thus, in general not applicable to the existing biosensors. Further, only a small number of redox mediators are available which, on one hand, comprise long-term stable, non-toxic, and insoluble properties and, on the other hand, exhibit the desired low working potential.

Alternatively, a number of technical solutions have been provided which may allow determining the effect of the interferents comprised in the body fluid onto the biosensor.

Firstly, ideas have been proposed which are related to a method of observing a dependency of the current in the biosensor on the applied electrical potential in order to be able to deduct the presence and, preferably, the amount of the interferent. However, known methods tend to provide ambiguous results and are, generally, not applicable in case more than one kind of interferent may be present.

Secondly, it may be promising to provide an interferent electrode, in particular, an additional working electrode being free of the enzyme. As a result, only the interferents, i.e. the other redox active substances within the body fluid, may, thus, be able to react with the additional working electrode. For this purpose, the additional working electrode may, preferably, comprise the same set-up and may be operated at the same working potential as the first working electrode. However, this proposal requires the production and operation of the additional working electrode together with supplementary circuit components, such as a bipotentiostat and one or more relay circuits.

U.S. Pat. No. 7,896,809 B2 discloses systems and methods for a continuous analyte sensor, such as a continuous glucose sensor. One such system utilizes first and second working electrodes to measure analyte or non-analyte related signal, both of which electrode include an interference domain.

U.S. Pat. No. 7,653,492 B2 discloses a method of reducing the effect of interfering compounds in a bodily fluid when measuring an analyte using an electrochemical sensor. In particular, the present method is applicable to electrochemical sensors where the sensor includes a substrate, first and second working electrodes, and a reference electrode and either the first and second or only the second working electrode include regions which are bare of enzyme. In this invention, an algorithm is described with mathematically corrects for the interference effect using the test strip embodiments of the present invention.

U.S. Pat. No. 6,121,009 A discloses a small diameter flexible electrode designed for subcutaneous in vivo amperometric monitoring of glucose. The electrode is designed to allow "one-point" in vivo calibration, i.e., to have zero output current at zero glucose concentration, even in the presence of other electroreactive species of serum or blood. The electrode is preferably three or four-layered, with the layers serially deposited within a recess upon the tip of a polyamide insulated gold wire. A first glucose concentration-to-current transducing layer is overcoated with an electrically insulating and glucose flux limiting layer (second layer) on which, optionally, an immobilized interference-eliminating horseradish peroxidase based film is deposited (third layer). An outer (fourth) layer is biocompatible.

US 2014/0158552 A1 discloses a method of measuring a component in blood, by which the amounts of blood cells and an interfering substance can be measured with high accuracy and high reliability and the amount of the component can be corrected accurately based on the amounts of the blood cells and the interfering substance. In a sensor for measuring a blood component, a first working electrode measures a current that flows during a redox reaction of a blood component, a second working electrode measures the amount of blood cells, and a third working electrode measures the amount of an interfering substance. Next, based on the measurement results, the amount of the blood component to be measured is corrected. Thus, more accurate and precise measurement of the amount of the blood component can be realized.

Problem to be Solved

It is therefore an objective of the present invention to provide a method for detecting an interferent contribution in a biosensor as well as a related method for validating an operation of a biosensor and/or for calibrating the biosensor, which at least partially avoid the shortcomings of known devices and methods of this kind and which at least partially address the above-mentioned challenges.

In particular, it is desired that the methods are capable of providing information about a presence of interferents within the body fluid and, preferably, about a magnitude of their influence on the measuring current in a simple and efficient way. In particular, a determination of a background current in the biosensor may be achieved simply and efficiently.

Further, it is desired that the methods according to the present invention may be implementable within sensor electronics architectures of standard biosensors and may, particularly, be applicable in existing biosensor systems.

SUMMARY OF THE INVENTION

This problem is solved by a method for detecting an interferent contribution in a biosensor and a method for validating an operation of a biosensor and/or for calibrating the biosensor, having the features of the independent claims. Preferred embodiments of the invention, which may be realized in an isolated way or in any arbitrary combination, are disclosed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a method for detecting an interferent contribution in a biosensor is disclosed. Herein, the biosensor has a first electrode, a second electrode, and a third electrode, wherein the first electrode and the second electrode are covered by a membrane, wherein the first electrode further includes an enzyme or wherein the first electrode is covered by an enzyme layer, and wherein the third electrode may also be covered by a membrane, which may, however, not necessarily be the case. In other terms, the first electrode, the second electrode, and the third electrode as used herein, may also be denominated as follows:
- the first electrode as a working electrode;
- the second electrode as a reference electrode; and
- the third electrode as an auxiliary electrode or as a counter electrode.

However other kinds of denominations may also be feasible.

Further according to the present invention, the first electrode, the second electrode, and the third electrode are connected via a potentiostat, wherein, in a normal operational mode, an electrical potential difference is applied via the potentiostat between the first electrode and the second electrode in a manner that the first electrode allows for oxidative processes and the third electrode allows for reductive processes. Herein, the method comprises the following method steps as listed as follows:
- a) switching from the normal operational mode to an interferent detection mode, wherein, in the interferent detection mode, the electrical potential difference is altered for a limited period of time in a manner that the third electrode allows for oxidative processes;
- b) measuring a current-voltage characteristic of the third electrode; and
- c) determining the interferent contribution in the biosensor by evaluating the current-voltage characteristic of the third electrode.

Herein, the indicated steps may, preferably, be performed in the given order, thereby starting with step a). However, any or all of the indicated steps, in particular steps b) and c), may also be preformed at least partially concurrently, such as over a definite period of time. Additionally, the indicated steps as a whole may also be repeated several times in order to achieve a subsequent detection of the interferent contribution in the biosensor, such as after a prespecified time or as a consequence of an occurrence of a prespecified event. Further, additional method steps, whether described herein or not, may be performed, too.

As generally used, the term "biosensor" may refer to an arbitrary device being configured for conducting at least one medical analysis. For this purpose, the biosensor may be an arbitrary device configured for performing at least one diagnostic purpose and, specifically, comprising at least one analyte sensor for performing the at least one medical analysis. The biosensor may, specifically, comprise an assembly of two or more components capable of interacting with each other, such as in order to perform one or more diagnostic purposes, such as in order to perform the medical analysis. Specifically, the two or more components may be capable of performing at least one detection of the at least one analyte in the body fluid and/or in order to contribute to the at least one detection of the at least one analyte in the body fluid. Generally, the biosensor may also be part of at least one of a sensor assembly, a sensor system, a sensor kit or a sensor device. Further, the biosensor may be connectable to an evaluation device, such as to an electronics unit.

In a particularly preferred embodiment of the present invention, the biosensor may be a fully or a partially implantable biosensor which may, particularly, be adapted for performing the detection of the analyte in the body fluid in a subcutaneous tissue, in particular, in an interstitial fluid. As used herein, the terms "implantable biosensor" or "transcutaneous biosensor" may refer to an arbitrary biosensor being adapted to be fully or at least partly arranged within the body tissue of the patient or the user. For this purpose, the biosensor may comprise an insertable portion. Herein, the term "insertable portion" may generally refer to a part or component of an element configured to be insertable into an arbitrary body tissue. Preferably, the biosensor may fully or partially comprise a biocompatible surface, i.e. a surface which may have as little detrimental effects on the user, the patient, or the body tissue as possible, at least during typical durations of use. For this purpose, the insertable portion of the biosensor may have a biocompatible surface. As an example, the biosensor, specifically the insertable portion thereof, may fully or partially be covered with at least one biocompatible membrane, such as at least one polymer membrane or gel membrane which, on one hand, may be permeable for the body fluid or at least for the analyte as comprised therein and which, on the other hand, retains sensor substances, such as one or more test chemicals within the sensor, thus preventing a migration thereof into the body tissue. Other parts or components of the biosensor may remain outside of the body tissue.

As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

As further used herein, the term "body fluid" may, generally, refer to a fluid, in particular a liquid, which may typically be present in a body or a body tissue of the user or the patient and/or which may be produced by the body of the user or the patient. Preferably, the body fluid may be selected from the group consisting of blood and interstitial fluid. However, additionally or alternatively, one or more other types of body fluids may be used, such as saliva, tear fluid, urine or other body fluids. During the detection of the at least one analyte, the body fluid may be present within the body or body tissue. Thus, the biosensor may, specifically, be configured for detecting the at least one analyte within the body tissue.

As further used herein, the term "analyte" may refer to an arbitrary element, component, or compound being present in the body fluid, wherein the presence and/or the concentration of the analyte may be of interest to the user, the patient, or to a medical staff, such as to a medical doctor. Particularly, the analyte may be or may comprise at least one arbitrary chemical substance or chemical compound which may participate in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may, in particular, be an analyte-specific detection. Without restricting further possible applications, the present invention is described in the following with particular reference to a monitoring of glucose in an interstitial fluid.

Besides the analyte, the body fluid may comprise additional substances which may be present in the body fluid and may, thus, be capable of influencing the detection of the analyte in the body fluid. This kind of additional substances within the body fluid are usually denominated as "interfering substances" or "interferents". In this regard, a distinction between "endogenous interferents" and "exogenous interferents" may be made. Whereas the endogenous interferents refer to additional substances which are generally considered as being naturally produced within the body, the exogenous interferents relate to additional substances which are, generally, only present within the body after having been supplied to the body fluid from the exterior of the body. In particular, the endogenous interferents may, particularly, include uric acid or cysteine, while the exogenous interferents may particularly include pharmaceuticals and drugs, such as ascorbic acid, acetylsalicylic acid, paracetamol, or acetaminophen. Moreover, one or more of the following substances may, depending on the circumstances be considered as one of the interferents, substances such as compounds with an electroactive acidic, amine or sulfhydryl groups, urea, peroxides, amino acids, amino acid precursors or break-down products, nitric oxide (NO), NO-donors, NO-precursors, bilirubin, creatinine, dopamine, ephedrine, ibuprofen, L-dopa, methyl dopa, salicylate, tetracycline, tolazamide, tolbutamide, electroactive species produced during cell metabolism and/or wound healing, and electroactive species that may arise during body pH changes. However, further kind of substances not mentioned here may also work as one of the interferents.

As further used herein, the term "measuring" refers to a process of generating at least one signal, in particular at least one measurement signal, which characterizes an outcome of the measurement. Specifically, the at least one signal may be or may comprise at least one electronic signal, such as at least one voltage signal and/or at least one current signal. The at least one signal may be or may comprise at least one analogue signal and/or may be or may comprise at least one digital signal. Especially in electrical systems, it may be required to apply a prespecified signal to a specific device in order to be able to record the desired measurement signal. By way of example, measuring a current signal may require the application of a voltage signal to the device, or vice-versa.

As further used herein, the term "determining" relates to a process of generating at least one representative result, such as a plurality of representative results, which may, in particular, be acquired by evaluating the at least one measurement signal, wherein the term "evaluating" may refer to an application of methods for displaying the at least one measurement signal and deriving the at least one representative result therefrom. In particular, a current-voltage characteristic of an electrode may be acquired, firstly, by applying a voltage between the electrode to be characterized and a reference electrode, such as provided by the potentiostat, and by, subsequently or concurrently, measuring the current signal as generated hereby and, secondly, by displaying the recorded values of the current signal versus the corresponding value of the applied voltage.

As further used herein, the term "detecting" refers to a process of establishing a presence and/or a quantity and/or a concentration of at least one substance in the body fluid, such as the analyte or the interferent. Thus, the detection may be or may comprise a qualitative detection, by which the presence of the at least one substance or the absence of the at least one substance may be derived, and/or may be or may comprise a quantitative detection, by which the quantity and/or the concentration of the at least one substance may be obtained.

As further used herein, the term "monitoring" refers to a process of continuously acquiring data and deriving desired information therefrom without user interaction. For this purpose, a plurality of measurement signals are generated and evaluated, wherefrom the desired information is determined. Herein, the plurality of measurement signals may be recorded within fixed or variable time intervals or, alternatively or in addition, at an occurrence of at least one prespecified event. In particular, the biosensor according to the present invention may, especially, be adapted for the continuous monitoring of one or more analytes, in particular of glucose, such as for managing, monitoring, and controlling a diabetes state.

The biosensor according to the present invention is an electrochemical sensor. As used herein, the term "electrochemical sensor" refers to a sensor being adapted for performing at least one electrochemical measurement, in particular a plurality or series of electrochemical measurements, in order to detect the at least one substance as comprised within the body fluid. Especially, the term "electrochemical measurement" refers to a detection of an electrochemically detectable property of the substance, such as an electrochemical detection reaction. Thus, for example, the electrochemical detection reaction may be detected by applying and comparing one or more electrode potentials. Specifically, the electrochemical sensor may be adapted to generate at least one electrical sensor signal which may directly or indirectly indicate a presence and/or an extent of the electrochemical detection reaction, such as at least one current signal and/or at least one voltage signal. The measurement may be a qualitative and/or a quantitative measurement. Still, other embodiments are feasible.

For this purpose, the electrochemical sensor as used herein is arranged in a fashion of an electrochemical cell and, thus, employs at least one pair of electrodes. As generally used, the term "electrode" refers to an entity of the test element which is adapted to contact the body fluid, either directly or via at least one semipermeable membrane or layer. With regard to the present invention, the electrode is covered by a membrane. Each electrode may be embodied in a fashion that an electrochemical reaction may occur at at least one surface of the electrode. In particular, the electrodes may be embodied in a manner that oxidative processes and/or reductive processes may take place at selected surfaces of the electrodes. Generally, the term "oxidative process" refers to a first chemical or biochemical reaction during which an electron is released from a first substance, such an atom, an ion, or a molecule, which is oxidized thereby. A further chemical or biochemical reaction by which a further substance may accept the released electron is, generally, denominated by the term "reductive process". Together, the first reaction and the further reaction may also be denominated as a "redox reaction". As a result, an electrical current, which generally relates to moving electrical charges, may be generated hereby. Further, the detailed course of the redox reaction may be influenced by an application of an electrical potential.

According to the present invention, the first electrode further includes an enzyme or, alternatively, is covered by an enzyme layer, wherein the enzyme or the enzyme layer acts here as a test chemistry, while the second electrode and the third electrode are maintained free from the test chemistry. Generally, the term "test chemistry" refers to an arbitrary material or a composition of materials being adapted to change at least one detectable property in the presence of the at least one analyte, wherein the detectable property is selected here from the above-mentioned electrochemically detectable property. Specifically, the at least one test chemistry may be a highly selective test chemistry, which only changes the property if the analyte is present in the sample of the body fluid applied to the test element, whereas no change occurs if the analyte may not be present. More preferably, the degree or change of the at least one property may be dependent on the concentration of the analyte in the body fluid, in order to allow for a quantitative detection of the analyte.

As used herein, the test chemistry may comprise one or more enzymes, such as glucose oxidase (GOD) and/or glucose dehydrogenase (GDH), preferably an enzyme which, by itself and/or in combination with other components of the detector substance, is adapted to perform an oxidative process or a reductive process with the at least one analyte to be detected. Additionally or alternatively, the test chemistry may comprise one or more auxiliary components, such as one or more co-enzymes and/or may comprise one or more redox mediators as mentioned above. Additionally, the test chemistry may comprise one or more dyes, which, preferably in interaction with the one or more enzymes, may change their color in the presence of the at least one analyte to be detected.

As already mentioned above, the course of the redox reaction which may occur in the biosensor may be influenced by application of an electrical potential. Thus, the detailed course of the redox reaction may be detected here by comparing one or more electrode potentials, in particular an electrical potential difference between the first electrode and the second electrode. For this purpose, the first electrode, the second electrode, and the third electrode of the biosensor are connected via a potentiostat. As used herein, the term "potentiostat" refers to an electronic device which is adapted for adjusting and/or measuring the electrical potential difference between the first electrode and the second electrode in the electrochemical cell. For this purpose, the potentiostat is implemented in order to be capable of injecting a current into the electrochemical cell through the third electrode, which is, for this reason, also denoted as the auxiliary electrode or the counter electrode. This setup of the potentiostat allows both adjusting the electrical potential difference between the first electrode and the second electrode within the electrochemical cell and, alternatively or in addition, measuring the current flow between the first electrode and the third electrode. Among further advantages, the potentiostat, thus, allows measuring the voltage in a practically currentless manner, which may be described as a considerably high input impedance of the device which may attain a value in the G$\Omega$ range. Additionally, the potentiostat may equally be employed for measuring the current, whereby no potential drop may occur due to an active current regulation as performed by the device.

As a result, the potentiostat is employed here for measuring the current-voltage characteristic of the third electrode according to step b), which may preferably acquired by, firstly, applying a voltage between the first electrode and the second electrode and by, preferably simultaneously, measuring the current as generated thereby between the first electrode and the third electrode and, secondly, by displaying the recorded values of the current signal versus the corresponding value of the applied voltage.

Alternatively or in addition, the current-voltage characteristic of the third electrode may be measured by applying a galvanostatic method. For this purpose, a galvanostat may be used, wherein, as generally, the term "galvanostat" refers to a control and measuring device which is capable of maintaining the current through the electrochemical cell constant, particularly, in consequence of a very high internal resistance. Thus, by applying a prespecified current as provided by the galvanostat between the first electrode and the third electrode and by, preferably simultaneously, measuring the electrical potential difference between the first electrode and the second electrode, the current-voltage characteristic of the third electrode may equally be acquired.

Further during the performance of the method according to the present invention, the electrical potential difference which is applied to the electrochemical cell is subject to an alteration in a predefined manner. As a result, it may be distinguished between two operational modes, which are denominated here as "normal operational mode" and "interferent detection mode". Accordingly, in the normal operational mode, the electrical potential difference is applied between the first electrode and the second electrode. Herein, the electrical potential difference between the first electrode and the second electrode within the electrochemical cell is adjusted in a fashion that oxidative processes take place at a surface of the first electrode while reductive processes take place at a surface of the third electrode. Herein, the term "normal operational mode" is employed since this kind of operational mode is related to a primary task of the biosensor, which is detecting the presence and/or the quantity and/or the concentration of the at least one analyte in the body fluid.

However, in contrast hereto, the interferent detection mode is used within the biosensor in order to detect the interferent contribution. Accordingly, the method according to the present invention comprises a process of switching from the normal operational mode to the interferent detection mode pursuant to step a). As used herein, the term "switching" refers to a process of moving from a first kind of action to a further kind of action, thereby providing the opportunity to return to the first kind of action. As will be explained later in more detail, the moving from one kind of action to another kind of action may be performed instantaneously, in particular after a limited period of time, or continuously, in particular during a limited period of time. As generally used, the term "limited period of time" may refer to a temporal duration which may last between a starting point and an end point. Herein, the starting point may refer to a point of time at which the further kind of action commences while the end point may relate to another point of time at which the further kind of action terminates. By way of example, the biosensor may be operated in the normal operational mode in order to detect the analyte within the body fluid. Prompted by a fixed time interval or by a variable time interval or, alternatively or in addition, by an occurrence of at least one prespecified event, the biosensor may then be operated in the interferent detection mode for detecting the interferent contribution. However, after the limited period of time, the biosensor returns into the normal operational mode in order to resume its primary task, which is the detection of the analyte within the body fluid.

For the purpose of detecting the interferent contribution, the electrical potential difference between the first electrode and the second electrode is altered during step a) for a limited period of time. As generally used, the term "altering" refers to modifying a property from a first value to at least one further value, such as a fixed further value or a range of further values. According to the present invention, in the interferent detection mode, the electrical potential difference between the first electrode and the second electrode is modified in a fashion that oxidative processes now take place at the surface of the third electrode. In addition, reductive processes may now take place at the surface of the first electrode, wherein, however, the location exact of the reductive processes may depend on the details of the electrode arrangement, the corresponding capacity of respective the respective electrodes, and the way of altering the electrical potential difference between the first electrode and the second electrode. Irrespective the particular embodiment, the oxidative processes and the reductive processes may proceed in a manner that, in any case, an electrical circuit within the electrode arrangement can be closed, in particular, by observing a negative current through the first electrode. As described below in more detail, an application of at least one potential step may, thus, result in a negative charging current. Consequently, a negative potential step may result in an occurrence of charging currents at the first electrode while reductive processes may already take place at the third electrode. Thus, the electrical potential between the first electrode and the second electrode may now exhibit a reversed polarity with respect to the normal operational mode, wherein, however, the electrical potential may actively set back to the previous polarity or, alternatively or in addition, may be subject to a relaxation process in order to resume the previous polarity within the limited period of time or shortly thereafter.

As a result of this kind of arrangement, the biosensor may, in the interferent detection mode, not be capable of measuring any variables related to the analyte but may rather be adapted to measure variables which are related to the presence and/or the quantity and/or the concentration of the interferent in the body fluid. However, as already mentioned above, the biosensor returns after the limited period of time into the normal operational mode, such as by a reset and/or by a relaxation process, wherein the electrical potential between the first electrode and the second electrode may resume its normal polarity such that the biosensor may again be capable of measuring the variables which are related to the analyte.

In general, the switching from the normal operational mode to the interferent detection mode according to step a) may be implemented by a time-varying alteration of the electrical potential difference between the first electrode and the second electrode.

In a particularly preferred embodiment, the switching from the normal operational mode to the interferent detection mode may be implemented by an application of at least one potential step to the electrical potential difference between the first electrode and the second electrode. For this purpose, the potentiostat may preferably be used. However, other measures may also be feasible. As used herein, the term "potential step" may refer to an instantaneous impingement of the first electrode by an additional electrical potential which may be provided in form of an electric pulse. Thereby, a height of the potential step may be selected in order to define a current range which may be passed through by the application of this procedure. Herein, the additional electrical potential may exhibit a sign and a magnitude which may accomplish that, after the application of the potential step, the polarity of the first electrode may, at least prior to the active set-back to the previous polarity and/or prior to a completion of the relaxation process, exhibit a reversed sign with respect to the second electrode.

As already indicated above, a negative potential step may result in a negative charging current at the first electrode which may, after termination of the charging process, return into a positive current in accordance with the usual process of the biosensor. As a consequence, the observable current at the first electrode may sweep through the negative current range until it may, depending on the concentration of the analyte, return to the positive current range. Similarly, the observable current at the third electrode may sweep through the positive current range until it may, depending on the concentration of the analyte, return to the negative current range. Thus, the current at the counter electrode is generated depending on a presence and a concentration of oxidizable substance which may be provided by the analyte and/or the interferent. In this manner, the current-voltage characteristic of the third electrode may, preferably, be accomplished. In addition, a zero-current transition, which will be described later in more detail, may, thus, be obtained.

As a result of this treatment, the biosensor may now be capable of detecting the variables related to the interferent in the body fluid, in particular, measuring the current-voltage characteristic of the third electrode according to step b). Following the application of the potential step, the first electrode which has been unbalanced hereby, may, thus, return to the normal operational mode within the limited period of time, in particular through the above-mentioned relaxation process. A time constant RC which can be attributed to this particular effect, may depend on features of the first electrode, such as a thickness of the membrane. During the limited period of time, the current between the first electrode and the third electrode and the voltage of the third electrode may be measured, wherein the limited period of time may comprise a measuring period, such as a time interval which may last from 0.5 seconds to 20 seconds, preferably from 1 second to 10 seconds, which may, however, depend on the capacity of the electrodes involved.

In an alternative embodiment, the switching from the normal operational mode to the interferent detection mode may be implemented by a step-wise or a continuous alteration of the electrical potential difference during the limited period of time. Also, the potentiostat may preferably be used for this purpose. However, other measures may also be feasible. As used herein, the term "step-wise alteration" may, particularly, refer to a varying of the electrical potential by setting a number of increasing predefined amplitudes each of which may be constant over a limited duration, such as constant limited durations, wherein the term "continuous alteration" may, especially, refer to a continuously varying electrical potential whose amplitude may vary within a prespecified potential range. Preferably, the electrical potential difference may, thus, perform a potential scan, wherein the scan may commence at the starting point with the value of the electrical potential difference in the normal operating mode and, after the limited period of time, may finish at the end point with an altered value. By way of example, the electrical potential difference may be changed along an ascent with a continuous modification between the starting point and the end point. However, other kinds of temporal progression of the time-varying alternation of the electrical potential difference may also be possible. During the variation of the electrical potential in the course of the potential scan, both the current between the first electrode and the third electrode and the voltage of the third electrode may be measured during the limited period of time, wherein the limited period of time may comprise a time interval which may last from 1 minute to 30 minutes, preferably from 5 minutes to 15 minutes.

As a result, the potential scan may require a considerable amount of time, in particular, when compared to the preferred time intervals which may be applied for the measuring period which follows the application of the potential step as described above. This kind of performance can be explained by a typical approach that the potential scan may, preferably, be performed in a fashion that each time a steady-state of the biosensor may be accomplished before an actual measurement value may be recorded. Further, during the application of the potential scan it may be advantageous to ensure that a balance with regard to the redox reaction may be maintained as far as possible.

Further, by evaluating the current-voltage characteristic of the third electrode according to step c) the interferent contribution in the biosensor is determined. As used herein, the term "contribution" refers to a measurable effect being generated by the presence of the interferent within the body fluid, wherein the measurable effect may, preferably, be detectable in the current-voltage characteristic of the third electrode. In particular, the interferents which are or which comprise additional redox active substances that may be oxidized in a manner similar to the redox active substances related to the analyte may, thus, generate further electrons which may be detectable as an additional current. Since the additional current may even be obtained in an absence of the analyte, the additional current may also be denominated as "background current" or "zero current". As already mentioned above, a first kind of interferents may comprise additional redox active substances which may behave in the same manner as the redox mediator and can, thus, directly be oxidized at the first electrode, thereby providing the additional current portion. Alternatively or in addition, a further kind of interferents may react with an intermediate product as generated during the glucose reaction, such as hydrogen peroxide ($H_2O_2$), in a manner that the concentration of the intermediate product in the body fluid may decrease. As a result, the sensitivity of the potentiostat may decrease.

In a further preferred embodiment, the current-voltage characteristic of the third electrode may be evaluated during step c) in a particular manner as described below in order to detect a kind and/or a quantity of the interferent contribution in the biosensor.

Firstly, a position of the zero-current transition which may occur in the current-voltage characteristic of the third electrode may, preferably, be determined for this purpose. As used herein, the term "zero-current transition" refers to at least one observable voltage value in the current-voltage characteristic at which the current vanishes or, more specifically, experiences a transition through the zero-current axis in the current-voltage characteristic in a manner that the current changes from a negative current value to a positive current value or, vive-versa, from a positive current value to a negative current value. In particular, the presence or the absence of a specific kind of interferent being capable of influencing the position of the zero-current transition may, thus, be determined.

By way of example, in a case in which the oxidative processes and the reductive processes take place in an aqueous phase, such as in the case of a typical body fluid, which does not comprise an analyte, in case the third electrode is a gold electrode, an established zero-current transition may occur at a voltage of approximately 550 mV which is, generally, attributed to an oxidation of the water content within the aqueous phase at the gold electrode. However, other values for the zero-current transition may occur may be observable at other voltages for different kinds of third electrodes. On the contrary, in case the analyte glucose may be present in the aqueous phase, the presence of the glucose may be detectable by an observation that hydrogen peroxide ($H_2O_2$) which may result from a reaction of the enzyme glucose oxidase (GOD) can be oxidized at the first electrode at a voltage approximately 275 mV, wherein a different analyte may, however, be oxidized at a different voltage value. It may be noted that this kind of reaction may not take place at the third electrode due to a spatial separation of the third electrode which does not comprise an enzyme from the first electrode within the electrode arrangement of the biosensor. Further, in case a specific interferent may, in addition to the glucose, be present in the aqueous phase, the presence of the interferent may be detectable by an observation that the interferent may be oxidized at the first electrode at a voltage below the voltage value at which the analyte, the water and the electrode material may be oxidized. As a consequence, the position of the zero-current transition occurring in the current-voltage characteristic of the third electrode may, thus, preferably be located below the voltage at which the analyte is going to be oxidized at the first electrode. As will be further illustrated in the figures below, a value as derived from a displacement of the position of the zero-current transition in the current-voltage characteristic with respect to a default position of the voltage value may, thus, be used as a criterion for the kind of interferent being present within the electrochemical cell.

Further, the current-voltage characteristic of the third electrode may, additionally, exhibit at least one current plateau. As used herein, the term "current plateau" may refer to a specific behavior of the course of the current within the current-voltage characteristic, by which the current may attain a constant value or level over a limited voltage range, wherein the term "constant value" may relate to a variation of the current which may be limited to a limited current range, such as within a lower threshold and an upper threshold. Thus, alternatively or in addition, a current value of the at least one current plateau occurring in the current-voltage characteristic of the third electrode may further be determined. As could be observed in a number of samples, the current value of a typical current plateau which may occur in the current-voltage characteristic of the third electrode may assume a value from 0.1 nA to 20 nA, in particular from 0.5 nA to 10 nA. As a result, a quantity of the interferent which may be present within the electrochemical cell may, thus, be determined from an evaluation of the current value at the at least one current plateau.

Further, in case in which at least one further interferent may be capable of providing a contribution in the biosensor, at least one transition between two different current plateaus may, additionally, occur in the current-voltage characteristic of the third electrode at at least one specific voltage. Accordingly, the kind of the at least one further interferent may, thus, be determined by evaluating the at least one position of at the least one specific voltage at which the at least one voltage transition may be observable between two specific different current plateaus.

As already mentioned above, the biosensor as used herein may be a fully implantable biosensor or, alternatively, a partially implantable biosensor. In particular, the biosensor may be adapted for a continuous monitoring of the analyte in the body fluid, preferably for a continuous measurement of the analyte in a subcutaneous tissue, in particular in an interstitial fluid, such as blood. However, other kinds of biosensors as well as of applications of the biosensor may also be feasible.

As further mentioned above, the analyte may, preferably, comprise glucose, wherein the enzyme may be glucose oxidase (GOD). Alternatively, other kinds of enzymes, such as glucose dehydrogenase (GDH), may also be employed. Herein, the first electrode in the biosensor which serves as the working electrode may be adapted for performing the oxidative processes. Similarly, the third electrode which serves as the counter electrode may be adapted for performing the reductive processes. Further, the second electrode serves as the reference electrode. As a result, a glucose level, such as the concentration of the glucose in the body fluid, may, thus, be determined by the oxidative processes at the working electrode. Consequently, the switching from the normal operational mode to the interferent detection mode according to step a) may, thus, comprise an application of an additional negative potential to the working electrode, in particular by using the potentiostat. In this regard, it may be emphasized that the additional negative potential being applied to the working electrode may be selected from a negative potential step comprising a single large negative value or from a potential scan with increasingly negative potential values in a step-wise or a continuously alternating manner.

Further, the interferent whose contribution may be detected according to the present invention may be one of an endogenous interferent and an exogenous interferent, wherein the interferent may be capable of affecting the analyte level. As will be illustrated below in the figures in more detail, the present method may, in particular, applicable for detecting the contribution of the endogenous interferent uric acid. Further possible examples may be found in the list of interferents provided above.

In this regard it may be emphasized that certain interferents, although being present within the body fluid, may not be detectable by the present method since they may not provide a contribution in a manner that their contribution may exhibit an influence onto the current-voltage characteristic of the third electrode. As an example, the endogenous substance cysteine turned out not to be a potential interferent at the concentration in which it was present in the body fluid as investigated. For further details, reference to the figures below made also made here.

Further, the present method may, in particular, be applicable for the detection of the contribution of exogenous interferents, wherein the exogenous interferent may, in particular, be a pharmaceutical compound, such as a medicament and/or a drug, or a metabolic product thereof. As particularly preferred examples, the contribution of the pharmaceutical substances ascorbic acid and/or acetylsalicylic acid and/or paracetamol may be detected by the present method. Further possible examples may be found in the list of interferents provided above.

Moreover, since the present method may, thus, not only be applicable for detecting the presence or absence of one or more pharmaceutical substances but also for determining a quantity and/or a concentration thereof, the present method may also be applicable for detecting and/or monitoring the quantity and/or the concentration of selected pharmaceutical substances which might exert an influence on the analyte level within the body fluid, in particular, on the blood glucose level. This additional opportunity may, thus, be employed for a more complete blood analysis in the managing, monitoring, and controlling the diabetes state of a patient.

In a further aspect of the present invention, a method for calibrating a biosensor is disclosed. This method comprises the steps of performing the method for detecting an interferent contribution in a biosensor as described above and/or below. In this regard, the method comprises, as at least one calibration measurement, the performance of the method for detecting the interferent contribution in the biosensor for at least one prespecified content, such as kind and concentration, of the at least one interferent and, preferably in a subsequent manner, storing the current-voltage characteristic of the third electrode or at least one characteristic value as derived thereof together with the corresponding interferent contribution, in particular, for further reference. In a particularly preferred embodiment, voltage values for a zero current in the current-voltage characteristic of the third electrode are determined as the at least one characteristic value. Alternatively or in addition, current values for a current plateau in the current-voltage characteristic of the third electrode are determined as the at least one characteristic value. Herein, one or more values determined for the current plateaus or, in particular, a value determined for the sum of the current plateaus at an electrical potential comparable to the electrical potential of the first electrode may, preferably, be employed for evaluating the zero current for being used in background current correction for calibration of the biosensor.

In the at least one calibration measurement, a general relationship between the at least one interferent content and the current-voltage characteristic of the third electrode or the at least one characteristic value thereof may be acquired. Said general relationship can, for example, be reported in the form of one or more calibration curves. In this connection, a general relationship is to be understood to mean a rule for a plurality of different values of the interferent content, which rule describes how said values of the interferent content may influence the current-voltage characteristic. The rule can be ascertained for a continuous range of values of the interferent concentration or else for a discontinuous range of interferent concentration values, for example a quantity of interferent concentration values spaced apart from one another. Accordingly, the general relationship can, for example, include a pointwise assignment of multiple interferent concentration values to, in each case, a corresponding influence on the current-voltage characteristic. Alternatively or additionally, the rule can also include a law in the form of an analytical function, which can also be referred to as a calibration curve or calibration function and which describes analytically the influence on the current-voltage characteristic by the interferent content.

The calibration measurement can, for example, be carried out by detecting, in each case, at least current-voltage characteristic in a plurality of test samples or calibration samples in which the interferent content is known. For example, it is possible to prepare test samples which have a definite concentration of a known interferent. With respect to said test samples, it is possible in each case to ascertain at least one current-voltage characteristic or a characteristic values as derived therefrom. In this way, it may be possible to determine a quantity of pairs of values, which each comprise the interferent content and the associated characteristic value. Said pairs of values can themselves describe the general relationship, or said general relationship can be ascertained from the pairs of values, for example by means of a fit. In some cases, it may be possible, for the general relationship to be described by a straight line, the slope and axis intercept of which can be determined from the pairs of values by using an appropriate fit. Said straight line can then be used as a calibration curve. More complex calibration curves may also be possible, for example exponential functions and/or polynomials, which describe very well the relationship between the pairs of values.

The general relationship, more particularly the calibration curve or calibration function, can be stored in particular in at least one data storage, for example in a volatile and/or nonvolatile data storage, which may be connected to at least one evaluation unit, such as in form of a data processing device. Said evaluation unit can be configured to completely or partly carry out the method steps of the methods according to the present invention. The calibration measurement can also be carried out in the evaluation unit or, alternatively, independently therefrom.

In a further aspect of the present invention, a method for validating an operation of a biosensor is disclosed, wherein this method is mutatis mutandis similar compared to the method for calibrating the biosensor as described above. Herein, the method for validating the operation of the biosensor may, particularly, be employed for a failsafe operation of the biosensor. As generally used, the term "failsafe operation" refers to an operational mode of the biosensor in which, in an event of a failure of the biosensor, the biosensor may, nevertheless responds in a way that might provide at least one reliable characteristic value, in particular, during the application of the continuous glucose monitoring. Alternatively or in addition, the method for validating the operation of the biosensor may, further, be employed for supplementing measurement values in an event in which no current measurement value may be provided by the biosensor for any reason but may still be required for the continuous glucose monitoring. In this regard, the general relationship between the at least one interferent content and the current-voltage characteristic of the third electrode or the at least one characteristic value thereof as described above may be employed in a similar fashion.

The methods according to the present invention exhibit a number of advantages with respect to the prior art. Instead of employing inadequate technical solutions for reducing the effect of the interferents the effect which the interferents that are present in the body fluid may exert onto the biosensor are actively detected. Hereby, the proposed methods of observing the dependency between the current and the electrical potential in the biosensor allow deducting the presence and, preferably, the amount of the interferent in an unambiguous way and are, generally, applicable in case of more than one kind of interferent. Further, neither additional working electrodes, such as electrodes being free of a reagent, nor supplementary circuit components, such as a bipotentiostat and one or more relay circuits, are required. Thus, the present methods may be implementable within sensor electronics architectures of standard biosensors and may, in particular, be applicable in already existing biosensor systems.

Summarizing, the following embodiments are potential embodiments of the present invention. Other embodiments, however, are feasible.

Embodiment 1

A method for detecting an interferent contribution in a biosensor, wherein the biosensor has a first electrode, a second electrode, and a third electrode, wherein the first electrode and the second electrode are covered by a membrane, wherein the first electrode further includes an enzyme or wherein the first electrode is covered by an enzyme layer, wherein the first electrode, the second electrode, and the third electrode are connected via a potentiostat, wherein, in a normal operational mode, via the potentiostat an electrical potential difference is applied between the first electrode and the second electrode in a manner that the first electrode allows for oxidative processes and the third electrode allows for reductive processes, the method comprising the steps of:

a) switching from the normal operational mode to an interferent detection mode, wherein, in the interferent detection mode, the electrical potential difference between the first electrode and the second electrode is altered for a limited period of time in a manner that the third electrode allows for oxidative processes;
b) measuring a current-voltage characteristic of the third electrode; and
c) determining the interferent contribution in the biosensor by evaluating the current-voltage characteristic of the third electrode.

Embodiment 2

The method according to the preceding Embodiment, wherein the switching from the normal operational mode to the interferent detection mode according to step a) comprises a time-varying alteration of the electrical potential difference during the limited period of time by using the potentiostat.

Embodiment 3

The method according to the preceding Embodiment, wherein the continuous alteration of the electrical potential difference comprises step-wise or continuously varying the electrical potential difference within a prespecified potential range.

Embodiment 4

The method according to the preceding Embodiment, wherein the continuously varying of the electrical potential difference comprises changing the electrical potential difference along a predefined potential ascent with step-wise or a continuous modification between a starting point and an end point of the prespecified potential range.

Embodiment 5

The method according to any one of the three preceding Embodiments, wherein the measuring of the current-voltage characteristic of the third electrode according to step b) comprises measuring the current between the first electrode and the third electrode and measuring the voltage of the third electrode during the limited period of time.

Embodiment 6

The method according to the preceding Embodiment, wherein the limited period of time lasts from 1 minute to 30 minutes.

Embodiment 7

The method according to the preceding Embodiment, wherein the limited period of time lasts from 5 minutes to 15 minutes.

Embodiment 8

The method according to any one of the preceding Embodiments, wherein the switching from the normal operational mode to the interferent detection mode according to step a) comprises an application of at least one potential step to the electrical potential difference between the first electrode and the second electrode by using the potentiostat.

Embodiment 9

The method according to the preceding Embodiment, wherein the measuring of the current-voltage characteristic of the third electrode according to step b) comprises measuring the current between the first electrode and the third electrode and measuring the voltage of the third electrode during a measuring period following the application of the potential step.

Embodiment 10

The method according to the preceding Embodiment, wherein the measuring period following the application of the potential step lasts from 0.5 seconds to 20 seconds.

Embodiment 11

The method according to the preceding Embodiment, wherein the measuring period following the application of the potential step lasts from 1 second to 10 seconds.

Embodiment 12

The method according to any one of the preceding Embodiments, wherein a position of a zero-current transition occurring in the current-voltage characteristic of the third electrode is determined at a potential of the first electrode.

Embodiment 13

The method according to the preceding Embodiment, wherein a kind of the interferent is determined by evaluating the position of the zero-current transition at the potential of the first electrode.

Embodiment 14

The method according to the preceding Embodiment, wherein an analyte is known to exhibit a zero-current transition in the absence of the kind of the interferent at a default position, wherein the voltage value of the default position differs from the voltage value of the position of the zero-current transition of the kind of the interferent.

Embodiment 15

The method according to the preceding Embodiment, wherein a value derived from a displacement of the position of the zero-current transition in the current-voltage characteristic with respect to the default position is used as a criterion for the kind of interferent.

Embodiment 16

The method according to any one of the preceding Embodiments, whereto in a current value of at least one current plateau which occurs in the current-voltage characteristic of the third electrode is further determined at the potential of the first electrode.

Embodiment 17

The method according to the preceding Embodiment, wherein a quantity of the interferent is determined by evaluating the current value at the current plateau at the potential of the first electrode.

Embodiment 18

The method according to any one of the two preceding Embodiments, wherein, in case at least one further interferent provides a contribution in the biosensor, at least one position of at least one voltage transition between two different current plateaus occurring in the current-voltage characteristic of the third electrode is determined at the potential of the first electrode.

Embodiment 19

The method according to the preceding Embodiment, wherein the kind of the at least one further interferent is determined by evaluating the at least one position of at the least one voltage transition between the two different current plateaus at the potential of the first electrode and/or by evaluating a value determined for the sum of the current plateaus at an electrical potential comparable to the electrical potential of the first electrode at the potential of the first electrode.

Embodiment 20

The method according to any one of the preceding Embodiments, wherein the biosensor is a fully implantable biosensor or a partially implantable biosensor.

Embodiment 21

The method according to the preceding Embodiment, wherein the biosensor is a biosensor for continuously monitoring an analyte.

Embodiment 22

The method according to the preceding Embodiment, wherein the biosensor is a biosensor for a continuous measurement of the analyte in a subcutaneous tissue.

Embodiment 23

The method according to the preceding Embodiment, wherein the biosensor is a biosensor for a continuous measurement of the analyte in a body fluid.

Embodiment 24

The method according to the preceding Embodiment, wherein the biosensor is a biosensor for a continuous measurement of the analyte in an interstitial fluid.

Embodiment 25

The method according to the preceding Embodiment, wherein the biosensor is a biosensor for a continuous measurement of the analyte in blood.

Embodiment 26

The method according to any one of the five preceding Embodiments, to wherein the analyte comprises glucose.

Embodiment 27

The method according to the preceding Embodiment, wherein the enzyme is one of glucose oxidase.

Embodiment 28

The method according to any one of the nine preceding Embodiments, wherein the interferent is one of an endogenous interferent and an exogenous interferent, wherein the interferent is capable of affecting a level of the analyte.

Embodiment 29

The method according to the preceding Embodiment, wherein the endogenous interferent is uric acid.

Embodiment 30

The method according to any one of the two preceding Embodiments, wherein exogenous interferent is a pharmaceutical compound or a metabolic product thereof.

Embodiment 31

The method according to the preceding Embodiment, wherein the exogenous interferent is one of ascorbic acid, acetylsalicylic acid, paracetamol, or acetaminophen.

Embodiment 32

A method for validating an operation of a biosensor and/or for calibrating the biosensor, comprising the steps of performing the method according to any one of the preceding Embodiments for at least one prespecified content of at least one interferent and storing at least one current-voltage characteristic of the third electrode or at least one characteristic value as derived thereof together with the corresponding interferent content.

Embodiment 33

The method according to the preceding Embodiment, wherein voltage values of a zero current and, in case at least one further interferent provides a contribution in the biosensor, at least one further voltage value of at least one voltage transition between two different current plateaus in the current-voltage characteristic of the third electrode are determined as the at least one characteristic value.

Embodiment 34

The method according to any one of the two preceding Embodiments, wherein current values for a current plateau in the current-voltage characteristic of the third electrode and/or a value determined for the sum of the current plateaus at an electrical potential comparable to the electrical potential of the first electrode are further determined as the at least one characteristic value.

Embodiment 35

The method according to any one of the three preceding Embodiments, wherein a relationship between the at least one interferent content and the current-voltage characteristic of the third electrode or the at least one characteristic value thereof is determined and stored as at least one calibration function.

Embodiment 36

The method according to the preceding Embodiment, wherein the at least one calibration function is stored in at least one data storage being connected to at least one evaluation unit, wherein the evaluation unit is configured to completely or partly carry out the method steps of the methods according to any one of the preceding Embodiments.

SHORT DESCRIPTION OF THE FIGURES

Further details of the invention may be derived from the following disclosure of preferred embodiments. The features of the embodiments may be realized in an isolated way or in any combination. The invention is not restricted to the embodiments. The embodiments are schematically depicted in the figures. Identical reference numbers in the figures refer to identical elements or functionally identical elements or elements corresponding to each other with regard to their functions.

Figure 9:
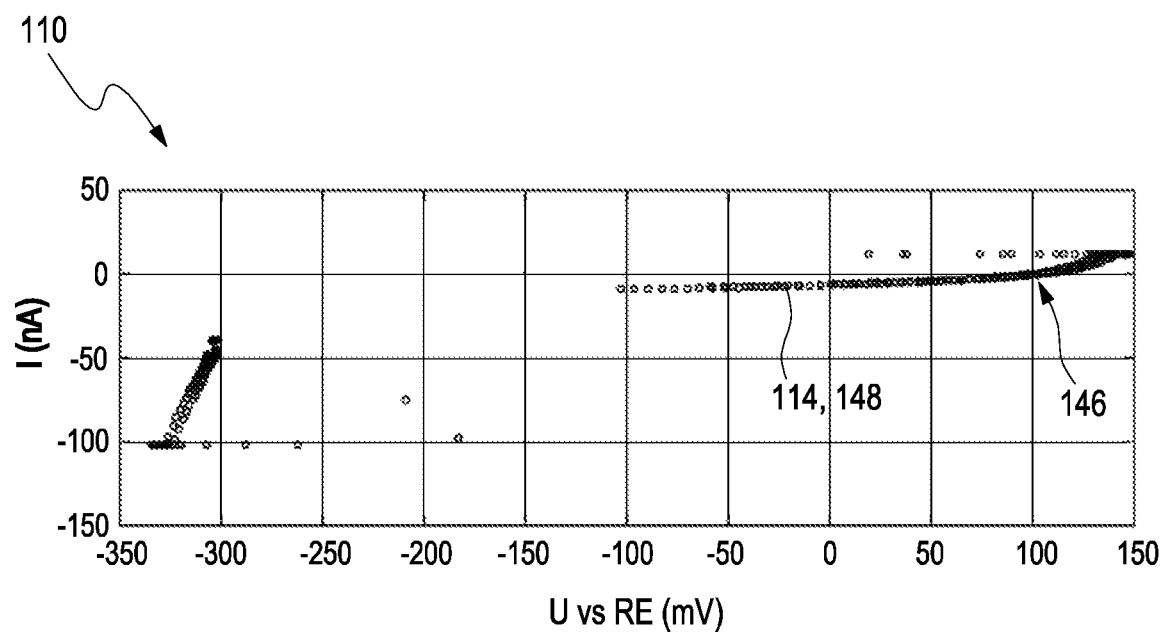
Figure 10:
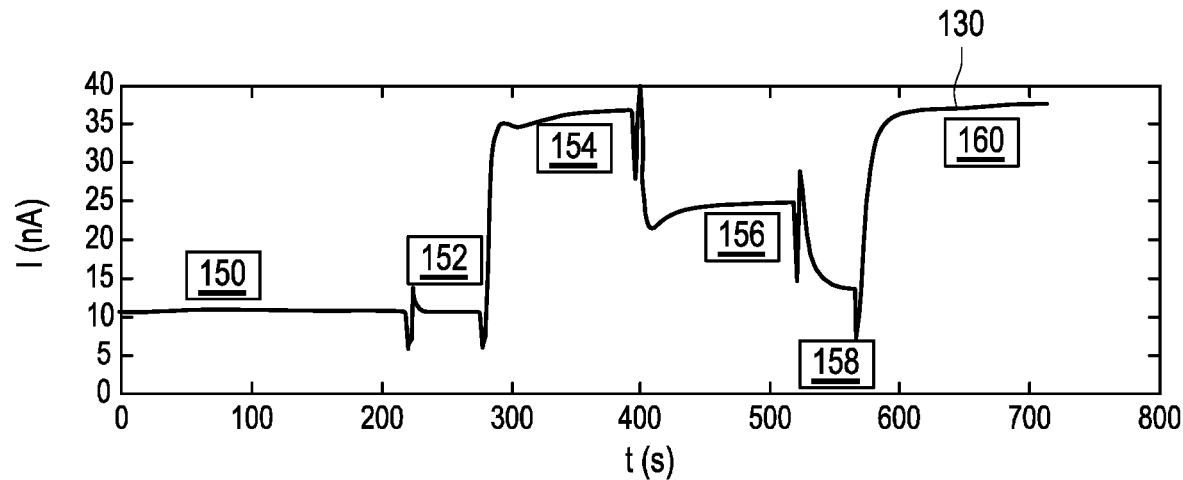

FIG. 9 illustrates the current-voltage characteristics of the third electrode measured in a further sample with the further endogenous interferent uric acid from a second source, wherein a potential step was applied by using the potentiostat; and FIG. 10 illustrates the time-dependent course of the current at the first electrode which was subsequently exposed to various samples comprising no interferent or different kinds of interferents.

DETAILED DESCRIPTION OF THE EMBODIMENTS

FIG. 1A illustrates current-voltage characteristics 110 of both a first electrode 112 and of a third electrode 114 in a biosensor, wherein the biosensor comprises an electrochemical cell which is arranged by the first electrode 112, a second electrode, and the third electrode 114. Herein, each of the current-voltage characteristics 110 were measured in a comparison sample 116, i.e. an artificial sample which did neither comprise any analyte, such as glucose, nor any interferent component. Herein, the current-voltage characteristics 110 were acquired by application of an interferent detection mode, in which, in contrast to the normal operational mode, the first electrode 112 may allow for reductive processes and the third electrode 114 allows for oxidative processes. For achieving the interferent detection mode, a potential scan 118 was applied by using a potentiostat, which means that an electrical potential difference between the first electrode 112 and the second electrode was step-wise altered for a limited period of time.

Figure 1:
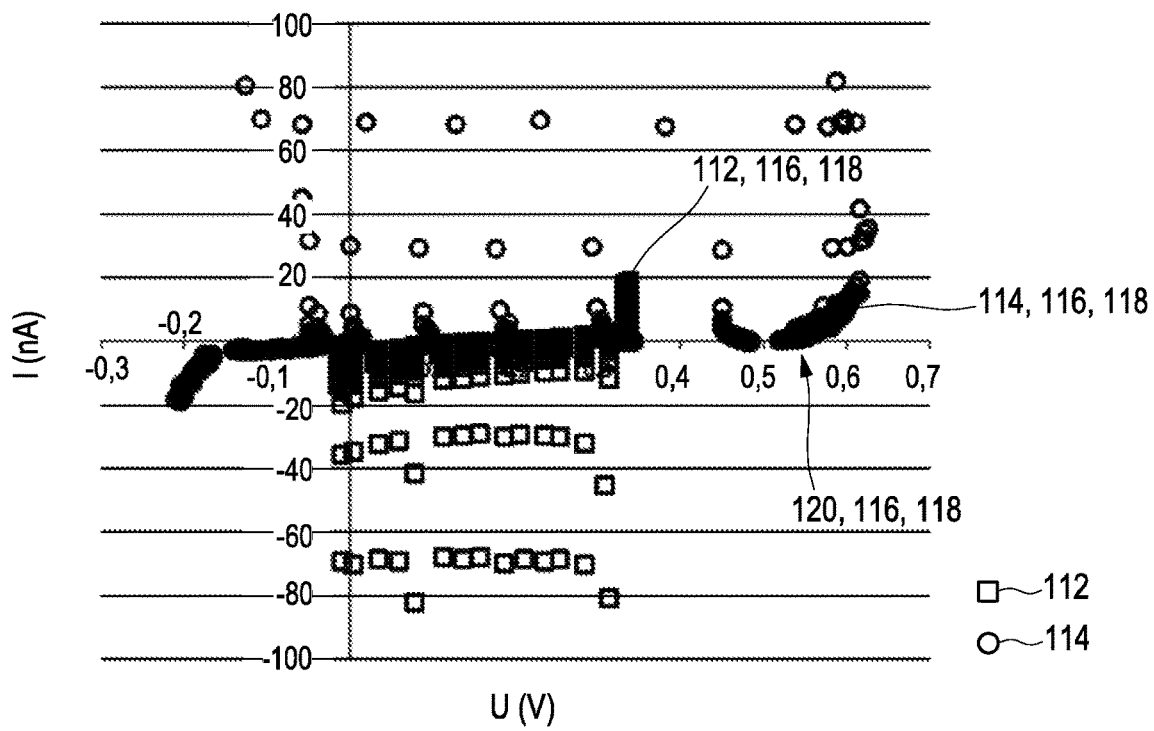
FIG. 1 illustrates current-voltage characteristics of both a first electrode and a third electrode, each measured in a comparison sample without interferent (FIG. 1A), wherein a step-wise alteration of an electrical potential difference between the first electrode and a second electrode was provided by using a potentiostat (FIGS. 1B to 1D)
Figure 1:
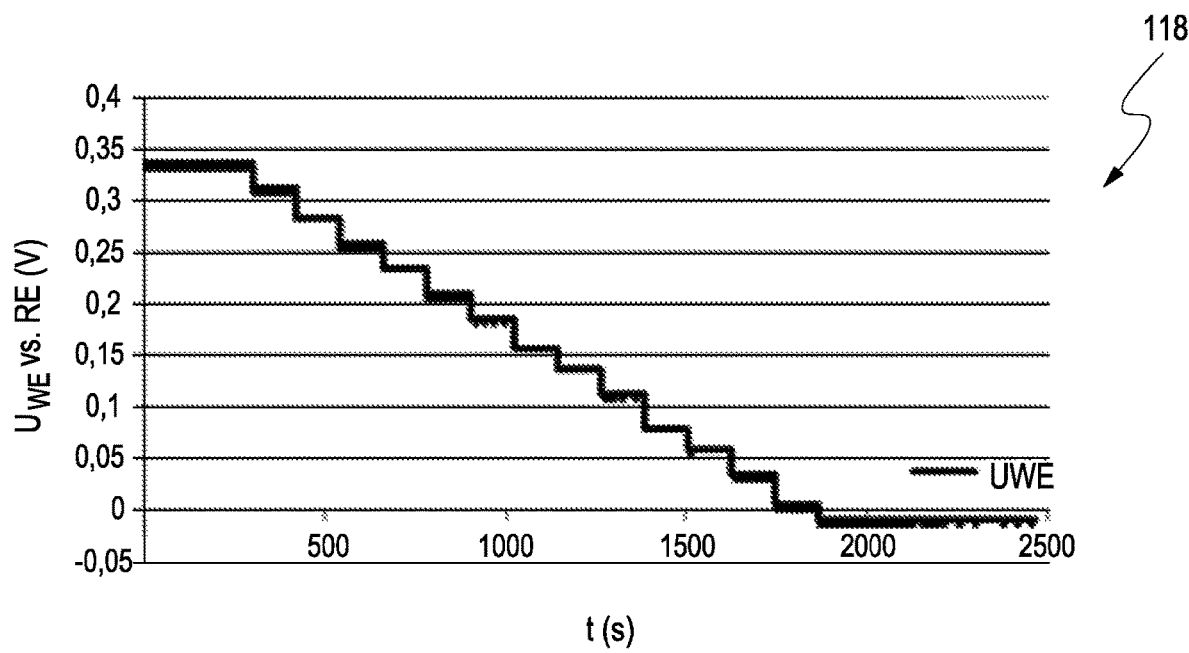
Figure 1:
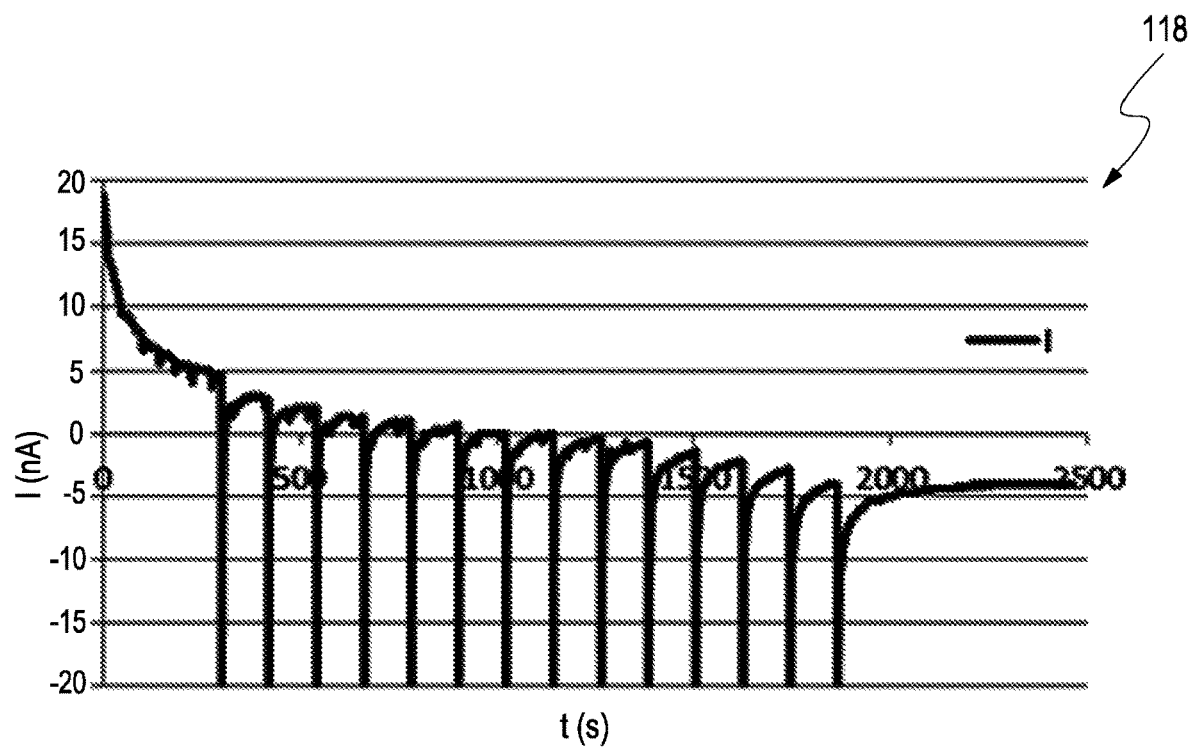
Figure 1:
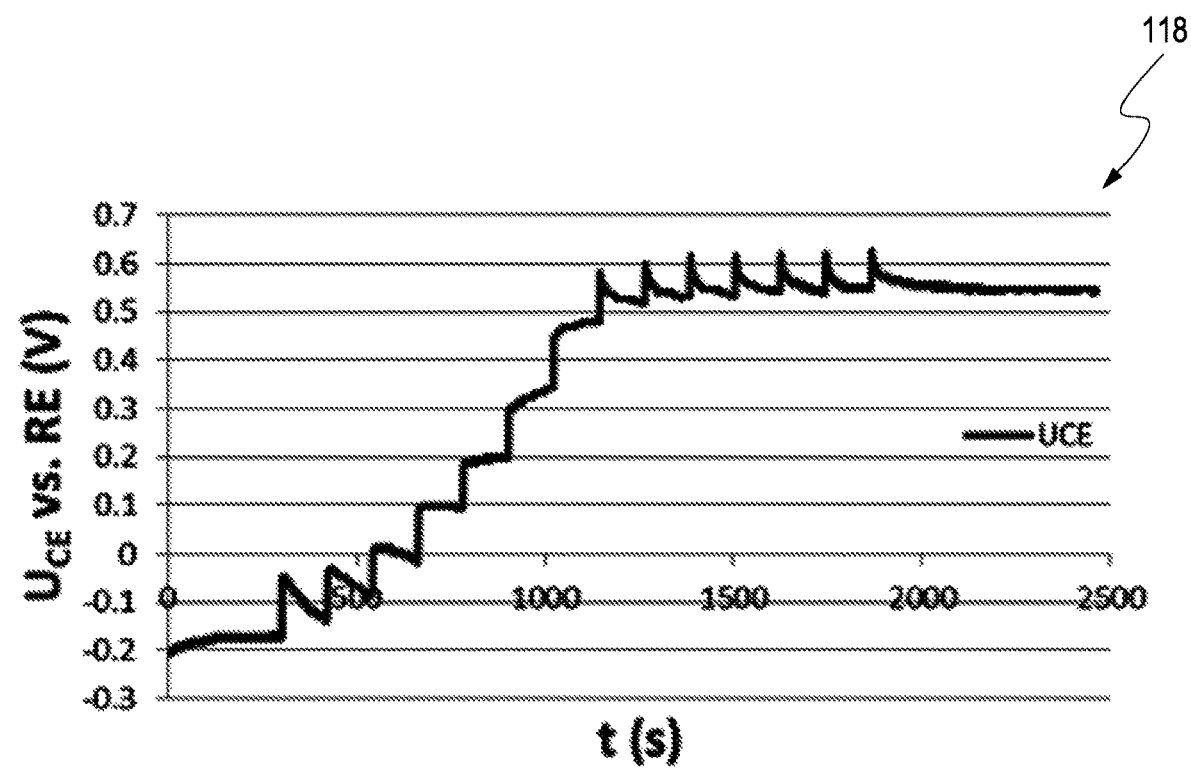

As can be derived from FIG. 1A, the current-voltage characteristic 110 of the third electrode 114 exhibits a zero-current transition which can be observed at a position 120 which corresponds to a default voltage of approximately 550 mV versus a reference electrode RE as provided by the potentiostat. This observation of the zero-current transition at the position 120 may be related to a typical case in which oxidative processes and reductive processes within the electrochemical cell of the biosensor may take place in an aqueous phase, wherein an established zero-current transition occurs at the default voltage which is, generally, attributed to an oxidation of the water content within the aqueous phase. Thus, the current-voltage characteristic 110 of the third electrode 114 as shown in FIG. 1 demonstrates that no interferent may be present in the comparison sample 116, at least no interferent which may exhibit an oxidation step occurring below the default voltage.

FIGS. 1B to 1D illustrate raw data which have been compiled in order to accomplish the presentation according to FIG. 1A. Herein, the respective data illustrating an application of the potential scan 118 are shown in the following figures:

FIG. 1B illustrates the potential difference in Volt (V) between the first electrode (working electrode, WE) 112 and the second electrode (reference electrode) versus time (s);

FIG. 1C illustrates the current I in nA through the third electrode (counter electrode) 114 versus time (s); and FIG. 1D illustrates the potential difference in Volt (V) between the first electrode (working electrode, WE) 112 and the third electrode (counter electrode) 114 versus time (s).

Figure 2:
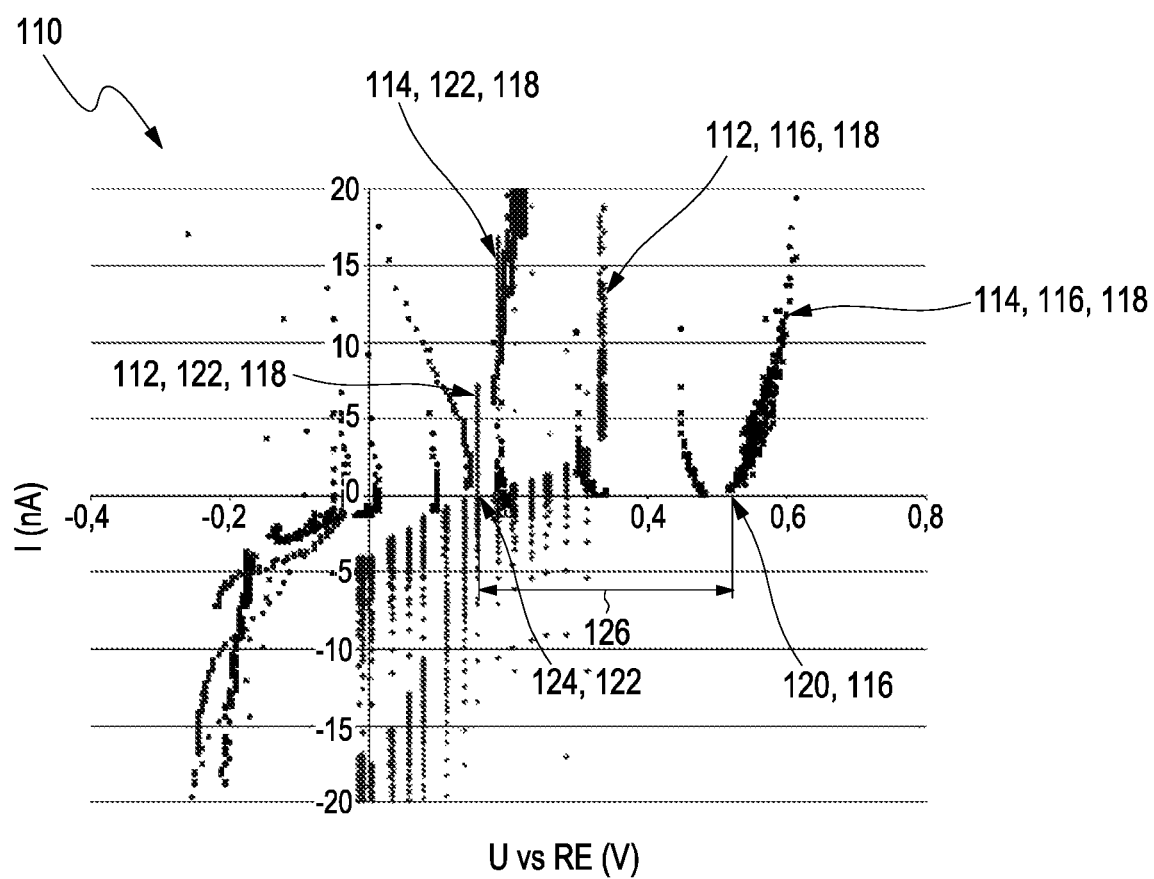
FIG. 2 illustrates the current-voltage characteristics of both the first electrode and the third electrode, each measured in a comparison sample without interferent and in a sample with the interferent uric acid, wherein a continuous alteration of the electrical potential difference between the first electrode and the second electrode was provided by using the potentiostat.

FIG. 2 illustrates the current-voltage characteristics 110 of both the first electrode 112 and the third electrode 114, each measured in a comparison sample 116 without interferent as well as in a sample 122 which comprises the endogenous interferent uric acid. As can be derived from FIG. 2, the current-voltage characteristic 110 of the third electrode 114 exhibits a zero-current transition which can be observed at the same position 120 for the comparison sample 116 as in FIG. 1 and at a displaced position 124 for the sample 122 comprising the endogenous interferent uric acid, thus leading to a displacement 126 of the zero-current transition. The displacement 126 between the positions 120, 124 of the zero-current transitions may be explained by the presence of the endogenous interferent uric acid in the sample 122 which may be more easily subject to an oxidation compared to the water content as comprised in both samples 116, 122. Again, the potentiostat was used here to perform the potential scan 118 during the interferent detection mode.

Figure 3:
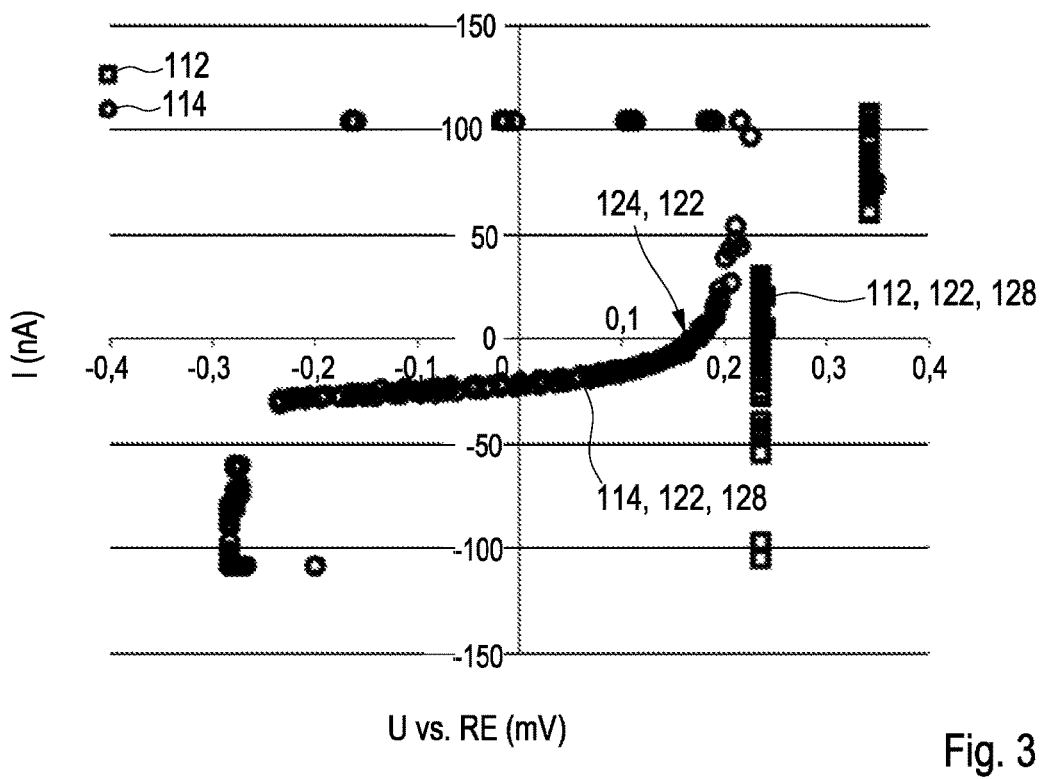
FIG. 3 illustrates the current-voltage characteristics of both the first electrode and the third electrode, each measured in a sample with the interferent uric acid, wherein a potential step was applied to the electrical potential difference by using the potentiostat.

FIG. 3 illustrates the current-voltage characteristics 110 of both the first electrode 112 and of the third electrode 114, each measured again in the sample 122 which comprises the endogenous interferent uric acid. In contrast to FIG. 2, a potential step 128 was applied here to the electrical potential difference between the first electrode 112 and the second electrode by using the potentiostat in order to achieve the interferent detection mode. Again, the current-voltage characteristic 110 of the third electrode 114 exhibits a zero-current transition at the displaced position 124 for the sample 122 comprising the endogenous interferent uric acid.

Consequently, achieving the interferent detection mode by application of the potential step 128 in FIG. 3, generally, provides the same results as the application of the potential scan 118 in FIG. 2. However, it may be emphasized that the application of the potential step 128 is capable of providing the same results within a considerably shorter period of time, such as 0.5 seconds to 20 seconds, compared to 1 minute to 30 minutes which may be typically used for the application of the potential scan 118 in order to maintain a steady-state of the electrochemical cell in the biosensor each time before an actual measurement value may be recorded.

Figure 4:
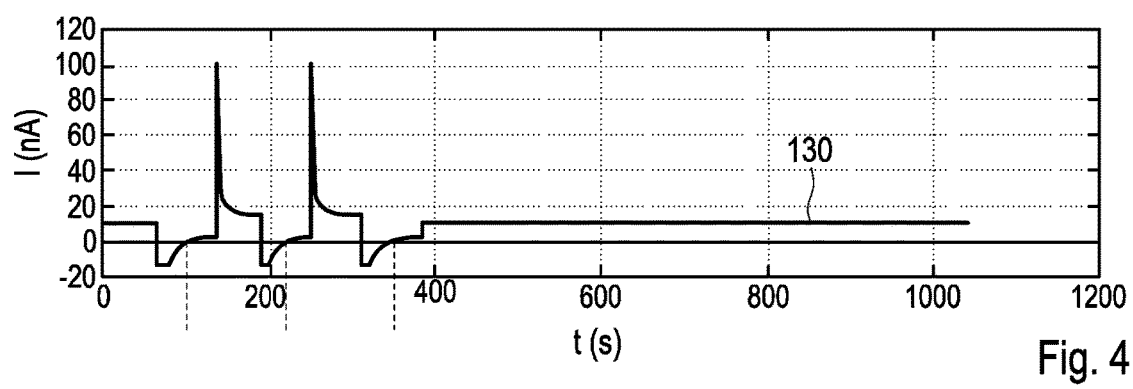
FIG. 4 illustrates a series of negative and positive potential steps as applied to a comparison sample without interferent in diagrams displaying the time-dependent course of the current at the first electrode (FIG. 4A) and of the voltage at the third electrode (FIG. 4B)
Figure 4:
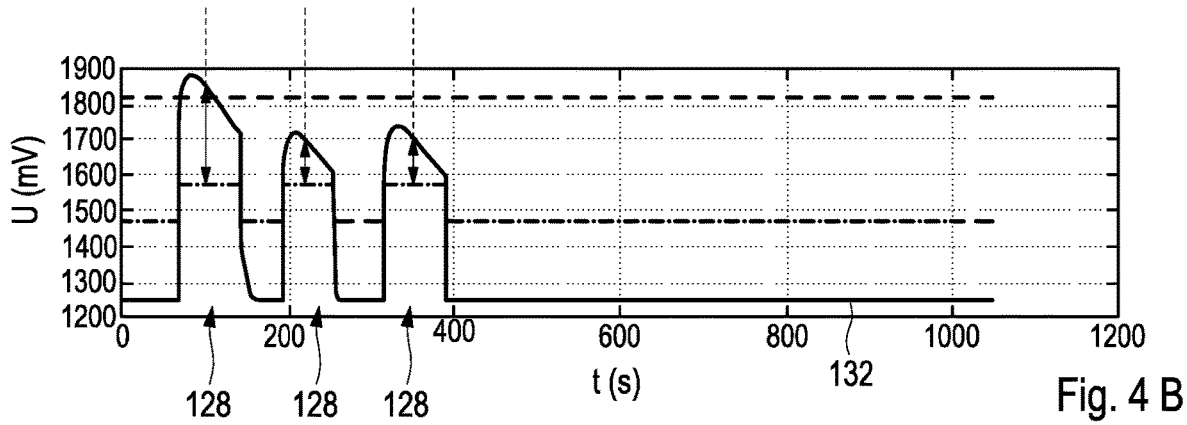

FIG. 4 illustrates an application of a series of negative and positive potential steps 128 to the electrochemical cell in the biosensor for measuring the comparison sample 116 comprising the analyte 10 mM glucose without interferent. Herein, FIG. 4A displays a diagram which exhibits a time-dependent course of the current 130 at the first electrode 112 while FIG. 4B shows a further diagram which displays the time-dependent course of the voltage 132 of the third electrode 114.

Figure 5:
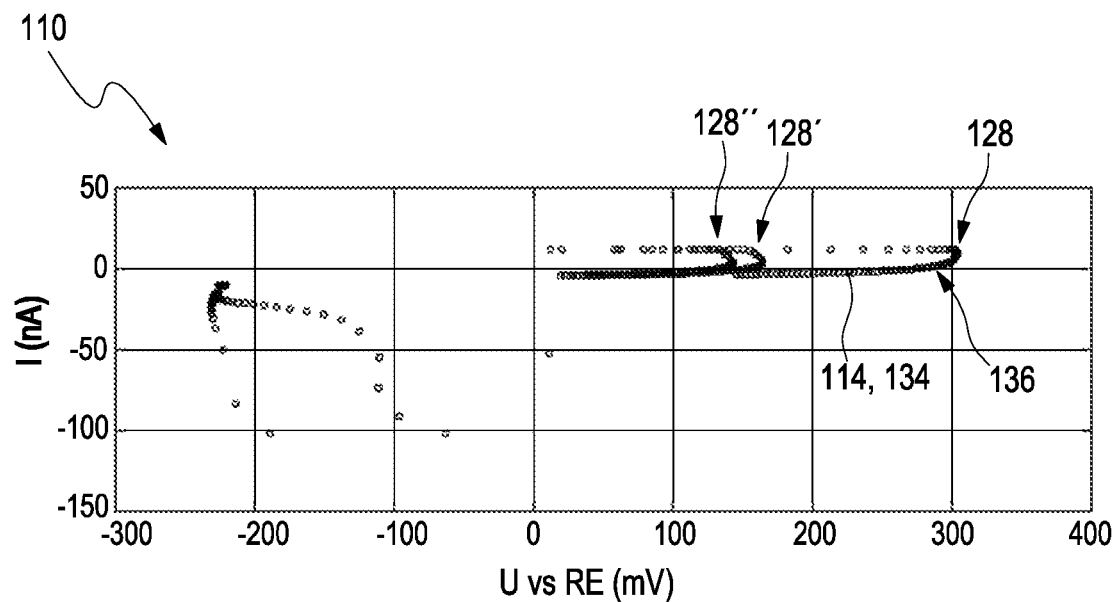
FIG. 5 illustrates the current-voltage characteristics of the third electrode measured in a sample without interferent, wherein subsequent potential steps were applied by using the potentiostat.
Figure 6:
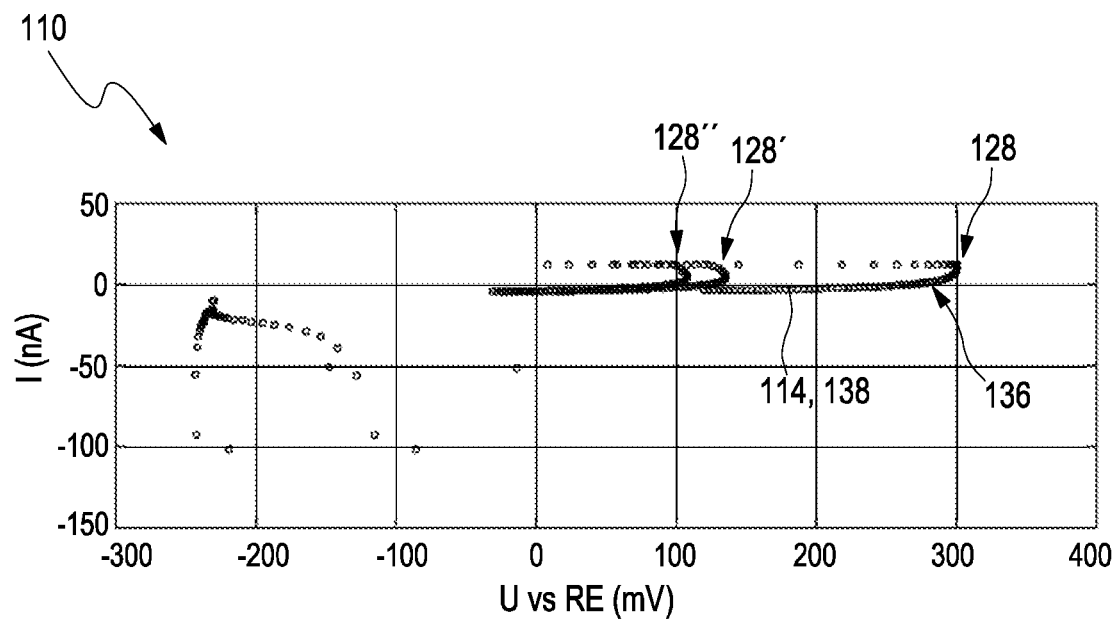
FIG. 6 illustrates the current-voltage characteristics of the third electrode measured in a sample with the endogenous interferent cysteine, wherein subsequent potential steps were applied by using the potentiostat.
Figure 7:
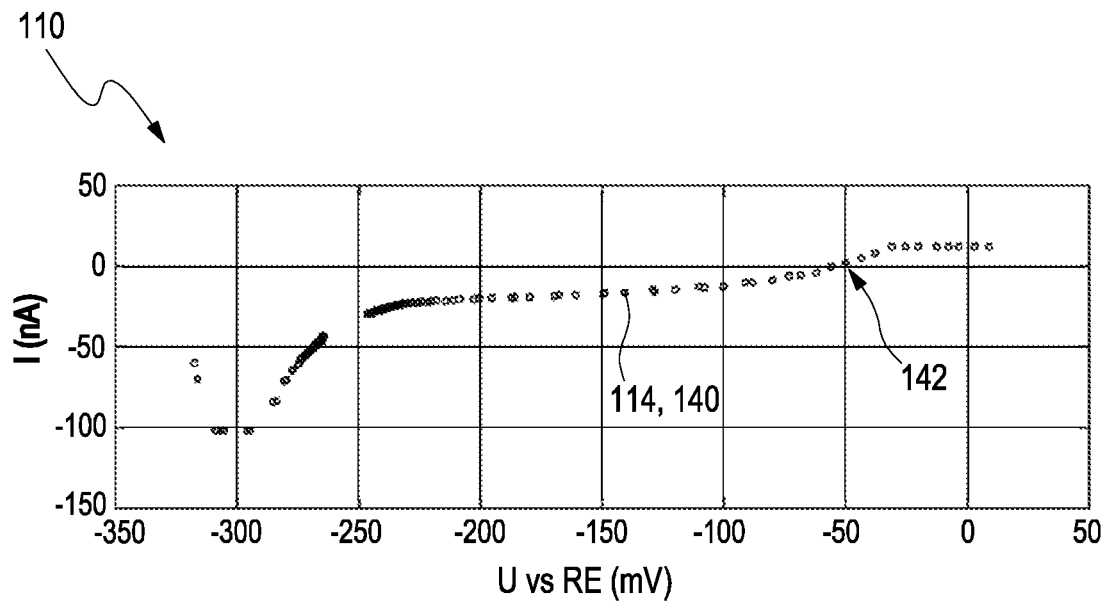
FIG. 7 illustrates the current-voltage characteristics of the third electrode measured in a sample with the exogenous interferent ascorbic acid, wherein a potential step was applied by using the potentiostat.
Figure 8:
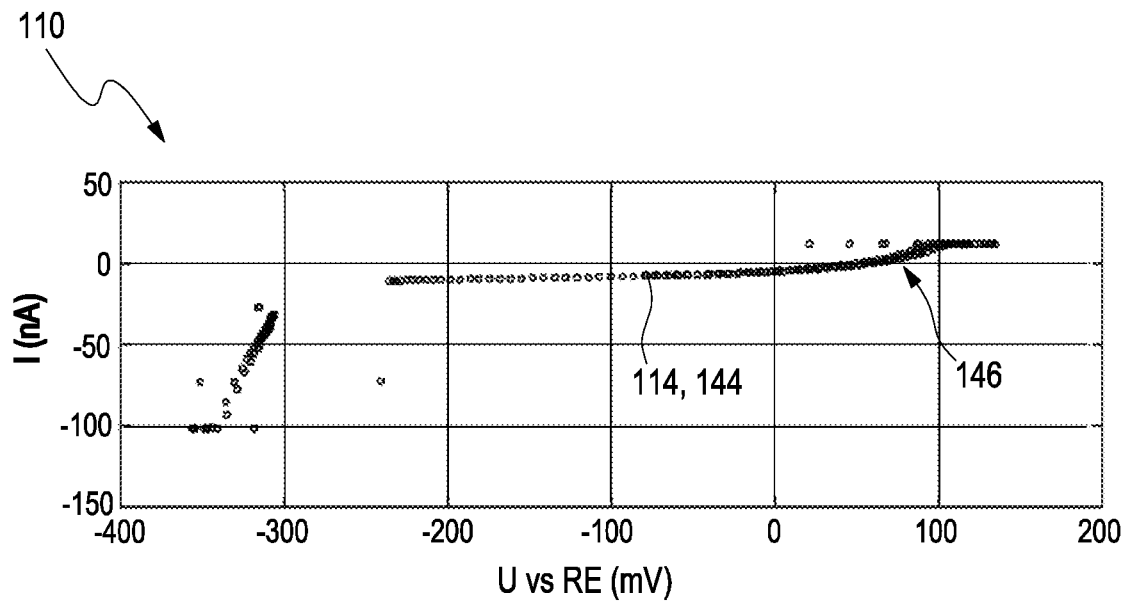
FIG. 8 illustrates the current-voltage characteristics of the third electrode measured in a sample with the further endogenous interferent uric acid from a first source, wherein a potential step was applied by using the potentiostat.

Each of the following FIGS. 5 to 9 illustrate the current-voltage characteristics 110 of the third electrode 114 as acquired after the application of one or more of the potential steps 128, 128', 128" to the electrochemical cell in the biosensor. Herein, the following samples were used:

FIG. 5: sample 134 comprising 10 mM glucose, i.e. no interferent, resulting in a position 136 of the zero-current transition at approximately 275 mV;

FIG. 6: sample 138 comprising 10 mM glucose and the endogenous interferent cysteine in a low concentration, thus, resulting in the same position 136 of the zero-current transition at approximately 275 mV;

FIG. 7: sample 140 comprising 10 mM glucose and the exogenous interferent ascorbic acid, resulting in a displaced position 142 of the zero-current transition at approximately −50 mV;

FIG. 8: sample 144 comprising 10 mM glucose and the further endogenous interferent uric acid from a first source, resulting in a further displaced position 146 of the zero-current transition at approximately 70-100 mV; and FIG. 9: further sample 148 comprising 10 mM glucose and the further endogenous interferent uric acid from a second source, resulting, however, in the same displaced position 146 of the zero-current transition at approximately 70-100 mV.

Finally, FIG. 10 illustrates the time-dependent course of the current 130 at the first electrode 112 which was subsequently exposed to various samples 150-160 either comprising no interferent or different kinds of interferents. Especially, the following samples 150-160 were used for this purpose:

sample 150 comprising 10 mM analyte glucose, i.e. no interferent;
sample 152 comprising the endogenous interferent cysteine in low concentration;
sample 154 comprising the exogenous interferent ascorbic acid;
sample 156 comprising the further endogenous interferent uric acid from the first source;
sample 158 comprising the further exogenous interferent salicylate; and
sample 160 comprising the further endogenous interferent uric acid from the second source.

LIST OF REFERENCE NUMBERS

110 current-voltage characteristic
112 first electrode
114 third electrode
116 comparison sample
118 potential scan
120 position of zero-current transition
122 sample comprising the endogenous interferent uric acid
124 displaced position of zero-current transition
126 displacement
128 potential step
130 time-dependent course of the current
132 time-dependent course of the voltage
134 sample comprising 10 mM glucose
136 position of the zero-current transition
138 sample comprising 10 mM glucose+cysteine
140 sample comprising 10 mM glucose+ascorbic acid
142 further displaced position of the zero-current transition
144 sample comprising 10 mM glucose+uric acid from a first source
146 further displaced position of the zero-current transition
148 sample comprising 10 mM glucose+uric acid from a second source
150 sample comprising 10 mM glucose
152 sample comprising cysteine
154 sample comprising ascorbic acid
156 sample comprising uric acid from a first source
158 sample comprising salicylate
160 sample comprising uric acid from a second source

The invention claimed is:

1. A method for detecting an interferent contribution by using an interferent detection mode within a biosensor, wherein the biosensor has a first electrode, a second electrode, and a third electrode, wherein the first electrode and the second electrode are covered by a membrane, wherein the first electrode further includes an enzyme or wherein the first electrode is covered by an enzyme layer, wherein the first electrode, the second electrode, and the third electrode are connected via a potentiostat, wherein, in a normal operational mode, via the potentiostat an electrical potential difference is applied between the first electrode and the second electrode in a manner that the first electrode allows for oxidative processes and the third electrode allows for reductive processes, the method comprising the steps of:

a) switching from the normal operational mode to an interferent detection mode, wherein, in the interferent detection mode, the electrical potential difference between the first electrode and the second electrode is altered for a limited period of time in a manner that the third electrode allows for oxidative processes;

b) measuring a current-voltage characteristic of the third electrode; and c) determining the interferent contribution by evaluating the current-voltage characteristic of the third electrode.

2. The method of claim 1, wherein the switching from the normal operational mode to the interferent detection mode according to step a) comprises a time-varying alteration of electrical potential difference during the limited period of time by using the potentiostat.

3. The method of claim 2, wherein the measuring of the current-voltage characteristic of the third electrode according to step b) comprises measuring the current between the first electrode and the third electrode and measuring the voltage of the third electrode during the limited period of time.

4. The method of claim 1, wherein the switching from the normal operational mode to the interferent detection mode according to step a) comprises an application of at least one potential step by using the potentiostat.

5. The method of claim 4, wherein the measuring of the current-voltage characteristic of the third electrode according to step b) comprises measuring the current between the first electrode and the third electrode and measuring the voltage of the third electrode during a measuring period following the application of the potential step.

6. The method of claim 1, wherein a position of a zero-current transition occurring in the current-voltage characteristic of the third electrode is determined at a potential of the first electrode.

7. The method of claim 6, wherein a kind of the interferent is determined by evaluating the position of the zero-current transition.

8. The method of claim 1, wherein a current value of at least one current plateau which occurs in the current-voltage characteristic of the third electrode is further determined.

9. The method of claim 8, wherein a quantity of the interferent is determined by evaluating the current value at the current plateau.

10. The method of claim 8, wherein, in case at least one further interferent provides a contribution in the biosensor, at least one position of at least one voltage transition between two different current plateaus occurring in the current-voltage characteristic of the third electrode is determined at the potential of the first electrode, wherein the kind of the at least one further interferent is determined by evaluating the position of the at least one voltage transition between the two different current plateaus.

11. The method of claim 1, wherein the biosensor is a fully or partially implantable biosensor for continuously monitoring an analyte.

12. The method of claim 1, wherein the analyte comprises glucose, and wherein the enzyme is glucose oxidase.

13. The method of claim 10, wherein the interferent is one of an endogenous interferent and an exogenous interferent, wherein the interferent is capable of affecting a level of the analyte.

14. The method of claim 13, wherein the exogenous interferent is a pharmaceutical compound or a metabolic product thereof.

15. A method of storing a value determined for the interferent contribution comprising the steps of performing the method of claim 1 for at least one prespecified content of at least one interferent and storing in a data storage at least one current-voltage characteristic of the third electrode, together with the corresponding interferent content.

16. The method of claim 9, wherein, in case at least one further interferent provides a contribution in the biosensor, at least one position of at least one voltage transition between two different current plateaus occurring in the current-voltage characteristic of the third electrode is determined at the potential of the first electrode, wherein the kind of the at least one further interferent is determined by evaluating the position of the at least one voltage transition between the two different current plateaus.

17. The method of claim 16, wherein the interferent is one of an endogenous interferent and an exogenous interferent, wherein the interferent is capable of affecting a level of the analyte.

18. The method of claim 17, wherein the exogenous interferent is a pharmaceutical compound or a metabolic product thereof.

\* \* \* \* \*